(12) United States Patent
Ali et al.

(10) Patent No.: US 7,399,826 B1
(45) Date of Patent: Jul. 15, 2008

(54) PEPTIDE FOR PROMOTING HEALING OF FRACTURES

(76) Inventors: Sadat M. Ali, 740 Lindsey La., Bolingbrook, IL (US) 60440; Ibrahim Al-Habdan, P.O. Box 40071, Alkhobar 31952 (SA)

( * ) Notice: Subject to any disclaimer, the term of this patent is extended or adjusted under 35 U.S.C. 154(b) by 11 days.

(21) Appl. No.: 10/577,739

(22) PCT Filed: Oct. 2, 2003

(86) PCT No.: PCT/US03/31078
§ 371 (c)(1),
(2), (4) Date: May 2, 2006

(87) PCT Pub. No.: WO2005/041998
PCT Pub. Date: May 12, 2005

(51) Int. Cl.
*A61K 38/04* (2006.01)
*A61K 38/00* (2006.01)

(52) U.S. Cl. .................................. 530/327; 514/14
(58) Field of Classification Search .......... 514/14
See application file for complete search history.

(56) References Cited

U.S. PATENT DOCUMENTS

| | | | |
|---|---|---|---|
| 4,086,221 A | 4/1978 | Sakakibara et al. |
| 4,167,557 A | 9/1979 | Goldstein |
| 4,959,455 A | 9/1990 | Clark et al. |
| 5,461,034 A | 10/1995 | Rodan et al. |
| 5,494,662 A | 2/1996 | Kohji et al. |
| 5,656,598 A | 8/1997 | Dunstan et al. |
| 5,663,146 A | 9/1997 | Bowers et al. |
| 5,681,818 A | 10/1997 | Spencer et al. |
| 5,698,521 A | 12/1997 | McKernan et al. |
| 5,698,672 A | 12/1997 | Labroo et al. |
| 5,750,651 A | 5/1998 | Opperman et al. |
| 5,880,094 A | 3/1999 | Tam |
| 6,194,380 B1 | 2/2001 | Kitamura et al. |
| 6,228,984 B1 | 5/2001 | Hinuma et al. |
| 6,258,778 B1 | 7/2001 | Rodgers et al. |
| 6,291,428 B1 | 9/2001 | Macaulay et al. |
| 6,300,127 B1 | 10/2001 | Hair et al. |
| 6,352,972 B1 | 3/2002 | Nimni et al. |
| 6,352,973 B1 | 3/2002 | Tam |
| 6,617,307 B1 | 9/2003 | Nishimura et al. |
| 2002/0077281 A1 | 6/2002 | Vickery |
| 2002/0090671 A1 | 7/2002 | Tam |
| 2002/0128202 A1 | 9/2002 | Curney et al. |
| 2003/0082784 A1 | 5/2003 | Nishimura et al. |

FOREIGN PATENT DOCUMENTS

| | | |
|---|---|---|
| EP | 128041 | 10/1995 |
| WO | WO 97/12036 | 4/1997 |
| WO | WO 99/12561 | 3/1999 |

*Primary Examiner*—Cecilia Tsang
*Assistant Examiner*—Maury Audet
(74) *Attorney, Agent, or Firm*—Richard C. Litman

(57) ABSTRACT

The peptide for promoting healing of fractures is a 13-amino acid peptide which is sequenced and synthesized in the laboratory. The peptide SHMSP has the sequence represented by the formula Met-Ile-Phe-Val-Lys-Thr-Leu-Thr-Gly-Lys-Thr-Ile-Leu. The peptide stimulates bone growth and accelerates healing of bone fractures. The peptide of the present invention has a low molecular weight. Consequently, it is absorbed in the body and excreted from the kidneys relatively easily.

6 Claims, No Drawings

US 7,399,826 B1

PEPTIDE FOR PROMOTING HEALING OF FRACTURES

TECHNICAL FIELD

The present invention relates to peptides which promote bone growth, and more particularly to a 13-amino acid polypeptide that accelerates healing of fractures.

BACKGROUND ART

Within the past few years, transforming growth factor-beta (TGF-β) was identified as a factor that stimulates osteoblasts in bone. The TGF-β molecules are dimers containing two identical polypeptide chains linked by disulfide bonds. Although TGF-β has been purified from several tissues and cell types, it is especially abundant in bones. TGF-β is postulated to be one of the local mediators of bone generation and resorption, because of its presence in large amounts in bone and cartilage, because cells with osteoblast and chondrocyte lineage increase replication after exposure to TGF-β, and because TGF-β regulates differentiation of skeletal precursor cells. However, clinical studies using TGF-β as a therapeutic agent have been hampered by its limited availability. TGF-$β_1$, for example, is usually purified from either human platelets, bone or soft tissues such as placenta and kidney. It is estimated that approximately one ton of bone is required to purify enough TGF-$β_1$ for a single therapeutic treatment. While small amounts of TGF-$β_1$ have been isolated as a recombinant protein which was processed and secreted by transfected mammalian cells into conditioned growth medium, the small amounts obtained and the high cost of production do not make this method of production commercially viable.

Bone morphogenetic protein (BMP) is a member of the transforming growth factor (TGF-β) family (Wozney, J. M. et al, Science, 242, 1528 (1988)), and its active form exists as a homodimer having a molecular weight of about 18 kilodaltons (kD). BMP has the function of acting on undifferentiated mesenchymal cells, inducing differentiation to chondroblasts and osteoblasts and effecting chondrogenesis and osteogenesis (Wang, E. A. et al. Proc. Natl. Acad. Sci. USA, 87, 2220 (1990)).

Although the BMPs are potent stimulators of bone formation in vitro and in vivo, there are disadvantages to their use as therapeutic agents to enhance bone healing. BMP's are relatively large, with a molecular weight of about 18 kD, and including between about 300 to 500 amino acid residues. Additionally, while human BMP is now produced using recombinant techniques, the cost of the protein remains high. Furthermore, receptors for the bone morphogenetic proteins have been identified in many tissues, and the BMPs themselves are expressed in a large variety of tissues in specific temporal and spatial patterns. This suggests that BMPs may have effects on many tissues in addition to bone, potentially limiting their usefulness as therapeutic agents when administered systemically. These disadvantages impose severe limitations to the development of BMPs as therapeutic agents.

U.S. Pat. No. 5,656,598, issued Aug. 12, 1997 to Dunstan et al., discloses therapeutic compositions for the prevention and treatment of pathological conditions involving bone and dental tissue. The Dunstan invention also provides a method to promote bone repair and/or growth for the treatment of pathological conditions involving bone tissue, for example, osteoporosis, Paget's disease, osteopetrosis, and periodontal disease and fracture repair, and healing of bone defects by administering FGF-1 to an animal or human in need of such treatment.

U.S. Pat. No. 6,258,778, issued Jul. 10, 2001 to Rodgers et al., discloses methods, kits, and compositions for enhancing bone, cartilage and cartilage repair, bone and prosthesis implantation, and attachment and fixation of cartilage and cartilage to bone or other tissues, and chondrocyte proliferation, comprising the administration of an effective amount of angiotensinogen, angiotensin I (AI), AI analogues, AI fragments and analogues thereof, angiotensin II (AII), AII analogues, AII fragments or analogues thereof, or AII $AT_2$ type 2 receptor agonists.

U.S. Pat. No. 6,352,972, issued Mar. 5, 2002 to Nimni et al., discloses a bone morphogenetic fusion protein and a method of preparation of the bone morphogenetic fusion protein. The bone morphogenetic fusion protein comprises a purification tag and a bone morphogenetic active fragment. A method of preparing bone morphogenetic fusion protein comprises purifying and renaturing bone morphogenetic protein to provide an active bone morphogenetic fusion protein preparation. Methods of use of the bone morphogenetic fusion protein are also provided.

U.S. Pat. No. 5,750,651, issued May 12, 1998 to Oppermann et al., discloses 1) osteogenic devices comprising a matrix containing osteogenic protein and methods of inducing endochondral bone growth in mammals using the devices; 2) amino acid sequence data, amino acid composition, solubility properties, structural features, homologies and various other data characterizing osteogenic proteins, 3) methods of producing osteogenic proteins using recombinant DNA technology, and 4) osteogenically and chondrogenically active synthetic protein constructs.

U.S. Pat. No. 5,461,034, issued Oct. 24, 1995 to Rodan et al., discloses a biochemically pure polypeptide(s), termed osteogenic growth polypeptide (OGP), which exhibits stimulatory effects on osteoblastic cells, in vivo bone formation, and hemopoietic reconstruction.

Other related patents include U.S. Patent Publication No. 2002/0077281, published Jun. 20, 2002 (fracture healing using PTHRP analogs); U.S. Patent Publication No. 2002/0090671, published Jul. 11, 2002 (bone stimulating factor); U.S. Patent Publication No. 2002/0128202, published Sep. 12, 2002. (stimulation of bone growth with thrombin peptide derivatives); U.S. Pat. No. 4,086,221, issued Apr. 25, 1978 to Sakakibara et al. (polypeptides and process for producing the same); U.S. Pat. No. 4,167,557, issued Sep. 11, 1979 to G. Goldstein (ubiquitous immunopoietic polypeptide [UBIP] and methods); U.S. Pat. No. 4,959,455, issued Sep. 25, 1990 to Clark et al. (primate hematopoietic growth factors IL-3 and pharmaceutical compositions); U.S. Pat. No. 5,494,662, issued Feb. 27, 1966 to Kohji et al. (stimulator for bone formation); U.S. Pat. No. 5,663,146, issued Sep. 2, 1997 to C. Bowers (polypeptide analogues having growth hormone releasing activity); U.S. Pat. No. 5,681,818, issued Oct. 28, 1997 to Spencer et al. (therapeutic uses of human somatomedin carrier proteins); U.S. Pat. No. 5,698,521, issued Dec. 16, 1997 to McKernan et al. (native calcitonin mimetics); U.S. Pat. No. 5,698,672, issued Dec. 16, 1997 to Labroo et al. (synthetic calcitonin mimetics); U.S. Pat. No. 5,880,094, issued Mar. 9, 1999 to C. S. Tam (polypeptides that stimulate bone growth); U.S. Pat. No. 6,194,380, issued Feb. 27, 2001 to Kitamura et al. (agents for promoting bone formation); U.S. Pat. No. 6,228,984, issued May 8, 2001 to Hinuma et al. (polypeptides, their production and use); U.S. Pat. No. 6,291,428, issued Sep. 18, 2001 to Macaulay et al. (peptides which promote bone-forming cell attraction and adhesion); U.S. Pat. No. 6,300,127, issued Oct. 9, 2001 to Hair et al. (bone mineralization proteins, DNA, vectors, expression systems); U.S. Pat. No. 6,352,973, issued Mar. 5, 2002 to C. S. Tam (bone stimulating factor); EP Patent No. 128,041, published Oct. 26, 1995 (polypeptides exhibiting skeletal growth factor activity); International Patent No. WO 97/12036, published Apr. 3, 1997 (bone stimulating factor); U.S. Pat. No. 6,617,307, issued Sep. 9, 2003 to Nishimura et al. (peptide and osteogenetic accelerator); and International Patent No. WO 99/12561, published Mar. 18, 1999 (fracture healing using PTHrp analogs).

None of the above inventions and patents, taken either singly or in combination, is seen to describe the instant invention as claimed. Thus a peptide for promoting healing of fractures solving the aforementioned problems is desired.

DISCLOSURE OF INVENTION

The peptide for promoting healing of fractures is a polypeptide which comprises an amino acid sequence represented by the formula Met-Ile-Phe-Val-Lys-Thr-Leu-Thr-Gly-Lys-Thr-Ile-Leu (SEQ ID No. 1), or an amide, ester, or salt thereof. The peptide is a 13-amino acid peptide which is sequenced and synthesized in the laboratory. The peptide stimulates bone growth and accelerates healing of bone fractures. The peptide of the present invention has a low molecular weight. Consequently, it is absorbed in the body and excreted from the kidneys relatively easily.

BEST MODES FOR CARRYING OUT THE INVENTION

The peptide for promoting healing of fractures of the present invention is termed Sadat-Habdan Mesenchymal Stimulating Peptide (SHMSP). SHMSP is a 13-amino acid peptide which is sequenced and synthesized in the laboratory. SHMSP stimulates bone growth and accelerates healing of bone fractures, spinal fusion, and bone production in osteoporosis. Since SHMSP is a small peptide, having a molecular weight of 1465 daltons, it is absorbed in the body and excreted from the kidneys relatively easily. Additionally, SHMSP is significantly less expensive and easier to synthesize than BMP. SHMSP has the sequence represented by the formula Met-Ile-Phe-Val-Lys-Thr-Leu-Thr-Gly-Lys-Thr-Ile-Leu (SEQ ID No 1). SHMSP is represented by SEQ ID NO 1, or its amide, ester, or salt. The information recorded in computer readable form is identical to the written sequence listing.

In the present specification, amino acid residues are represented by abbreviation symbols as follows:

Gly: L-glycine residue

Ile: L-isoleucine residue

Leu: L-leucine residue

Lys: L-lysine residue

Met: L-methionine residue

Phe: L-phenylalanine residue

Thr: L-threonine residue

Val: L-valine residue

Also in the present specification, the amino acid sequence of a peptide is written according to the conventional notation, with an amino group at the N-terminal appearing on the left hand of the sequence and carboxyl group at the C-terminal appearing on the right hand thereof.

The peptide of the present invention can be sequenced and synthesized in laboratory by using standard Fmoc chemistry (Fmoc chemistry refers to a method of solid phase peptide synthesis in which the α-amino group is temporarily protected by a base labile 9-fluorenylmethoxycarbonyl [Fmoc] protecting group). In a typical synthesis, the C-terminal amino acid residue of the peptide is linked to an insoluble support, typically a solvated polymer gel, via an acid labile linker. Suitable solid phase polymers include, but are not limited to, cross-linked polystyrene and polyethylene glycol (PEG) polymers. Suitable linkers include Wang, hydroxymethyl-phenoxy acetyl (HMPA), Rink acid, 2-Chlorotrityl chloride, and SASRIN. The linker provides a reversible linkage between the peptide chain and the solid support and protects the C-terminal %-carboxyl group. The α-amino group is protected by 9-fluorenylmethoxycarbonyl (Fmoc). Any side chains on the amino acid are typically protected by an acid labile protecting group. Protecting groups which may be used for the side chain functionalities of amino acids that are chemically compatible with Fmoc groups are well known in the art. After linking to the solid phase, the N-terminal group of the amino acid chain is deprotected, and an Fmoc protected amino acid residue desired next in the sequence is added to the chain by a suitable coupler, which activates the α-carboxyl group of the residue being added. Suitable couplers include carbodiimide couplers, preformed esters or symmetrical anhydrides, or acid halides. Successive deprotection and coupling cycles are used to build the whole peptide sequence.

For example, in order to synthesize the peptide of the present invention, an Fmoc protecting. group is attached to the α-amino group of leucine, which is then coupled to the solid phase support by a suitable linker. Then an Fmoc protecting group is attached to the N-terminal amino group of isoleucine, the Fmoc protecting group on the leucine residue is removed, and the isoleucine group is attached to the leucine by a suitable coupler. The deprotection-coupling cycle is repeated until all thirteen residues have been added to the chain.

The peptide is cleaved from the solid phase polymer resin and deprotected by treatment with trifluoracetic acid (TFA) with 2.5% H2O/2.5% ethanedithiol, which simultaneously removes the side chain protecting groups. Purification may be achieved by conventional methods, such as gel filtration and reverse phase HPLC (high performance liquid chromatography). Preferably, Beckman Gold HPLC system is used with 10 mm×250 mm C18 HPLC column, Buffer A being 0.1% TFA/H2O and Buffer B being 0.1% TFA/Acetonitrile. Analysis of the peptide should be conducted to determine the purity of the product and conformation of the structures. Suitable analysis techniques to verify that the desired peptide has been obtained include at least reverse-phase HPLC coupled with mass spectrometry, and may be further supplemented with sequencing of the amino acids.

Although the peptide of the present invention is preferably synthesized by Fmoc chemistry, the peptide may also be prepared by the t-Boc synthesis of Merrifield.

SHMSP can be used in mammals to treat bone fracture, in spinal fusion, and to promote bone growth in osteoporosis. Experimental studies in non-rodent and rodent animals have shown that SHMSP stimulates bone production. Although it is not yet clear, it is believed that SHMSP enhances bone production by stimulating osteoblasts for new bone formation and inhibiting the proliferation of chondroblasts. The following is one example of a study conducted on rabbits to determine the effectiveness of SHMSP on fracture healing.

TEST EXAMPLE

Ulnar osteotomies were carried out in forty, three-month-old New Zealand rabbits. Half of the rabbits were placed in a study group while the other half was placed in a control group. All the rabbits were anesthetized using intramuscular ketamine 35 mg/kg body weight mixed with Xylazine 5 mg/kg body weight and an ophthalmic band with gentamycin ophthalmic ointment. A dose of prophylactic intramuscular cefuraxmine 25 mg/kg body weight was also administered. The forelimb was shaved and prepped in a sterile fashion. Through a posterior incision, the muscles were retracted and the shaft of the ulna was identified. Osteotomy was carried out equidistant between the olecranon and the wrist joint. The osteotomy was irrigated with normal saline. The wound was closed in layers and dressed with betadine and opsite spray. The animals were kept together in similar conditions. On the third post-operative day, the study group was injected with about 2.5-5 mg/kg of the peptide, synthesized as described above, in 0.25 ml of sterile water around the osteotomy site, while the control group received 0.25 ml of normal saline at the osteotomy site. Every week, five rabbits in the control group and five in the study group were sacrificed and their limbs were dissected and stored in 2% formalin. The study was carried out for four weeks. The limbs were sent to an animal pathologist at the Animal Reference Lab at Salt Lake City, Utah after the fourth week.

The results demonstrated that SHMSP is effective in enhancing fracture healing. All rabbits tolerated the procedure well, as there were no wound infections or deaths. Radiographic analysis showed that the osteotomies in the study groups were all united by the beginning of the third week, whereas in the control group, the union was not complete even by the end of the fourth week. Histological evaluation indicated that there were apparent differences in the healing pattern of the study and control groups. The control group showed extensive cartilaginous response with little to no osteoid. The study group demonstrated much more osteoid and a sheet of new bone in and around the periosteal surface and across the medullary cavity.

The peptide of the present invention may be used singly for the purpose of preventing or treating bone fractures. The peptide may be fixed, mixed, solved, or suspended in a proper carrier or an aqueous solvent which can contain a variety of pharmacologically acceptable derivatives, such as a stabilizer, a preservative, a thickener, a solubilizer and the like. The carrier for fixing the peptide of the present invention is not particularly limited to any type, provided that it has compatibility to living bodies. Preferably, however, the carrier is a single dose carrier and a collagen matrix, such as DuraGen® (a trademark of Integra Lifesciences Corporation of Plainsboro, N.J.).

It is to be understood that the present invention is not limited to the embodiments described above, but encompasses any and all embodiments within the scope of the following claims.

---

---

We claim:

1. A synthesized peptide, comprising the amino acid sequence represented by the formula Met-Ile-Phe-Val-Lys-Thr-Leu-Thr-Gly-Lys-Thr-Ile-Leu (SEQ ID No 1), or an amide, ester, or salt thereof.

2. A method for achieving an effect in a patient, comprising administering an effective amount of the peptide of claim 1 to a patient, wherein the effect is promoting union of bone tissue in fracture, promoting bone growth in spinal fusion, or promoting bone growth in therapy for osteoporosis.

3. A pharmaceutical composition for enhancing bone repair comprising a therapeutically effective amount of a peptide having the amino acid sequence represented by the formula Met-Ile-Phe-Val-Lys-Thr-Leu-Thr-Gly-Lys-Thr-Ile-Leu (SEQ ID No 1) and a biocompatible carrier.

4. The pharmaceutical composition according to claim 3, wherein the carrier is a single dose carrier.

5. The pharmaceutical composition according to claim 3, wherein the carrier is a collagen matrix.

6. A method for enhancing bone repair in a mammal, comprising the administration of a therapeutically effective amount of a peptide having the amino acid sequence represented by the formula Met-Ile-Phe-Val-Lys-Thr-Leu-Thr-Gly-Lys-Thr-Ile-Leu (SEQ ID No 1).

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Met Ile Phe Val Lys Thr Leu Thr Gly Lys Thr Ile Leu
1               5                   10
```